United States Patent [19]

Augelli-Szafran

[11] Patent Number: 5,185,349
[45] Date of Patent: Feb. 9, 1993

[54] SUBSTITUTED AMIDE ACAT INHIBITORS LACTONE DERIVATIVES

[75] Inventor: Corinne E. Augelli-Szafran, Ypsilanti, Mich.

[73] Assignee: Warner-Lambert Company, Morris Plains, N.J.

[21] Appl. No.: 666,300

[22] Filed: Mar. 8, 1991

[51] Int. Cl.$^5$ .................. A01N 43/40; C07D 309/06
[52] U.S. Cl. ..................... 514/336; 514/459; 514/824; 546/268; 546/283; 549/271; 549/291; 549/321; 549/322
[58] Field of Search ............... 549/321, 322, 271, 291; 546/268, 283; 514/336, 459, 824

[56] References Cited

U.S. PATENT DOCUMENTS

| | | | |
|---|---|---|---|
| 3,130,203 | 4/1964 | Bächel et al. | 549/322 |
| 3,472,878 | 10/1969 | Bruderlein | 549/322 |
| 4,625,040 | 1/1986 | Georgiev et al. | 549/321 |
| 4,728,669 | 3/1988 | Chan | 549/321 |
| 4,774,334 | 9/1988 | Georgiev et al. | 549/321 |

FOREIGN PATENT DOCUMENTS

| | | | |
|---|---|---|---|
| 896658 | 6/1976 | Belgium | 549/291 |
| 1277262 | 9/1968 | Fed. Rep. of Germany | 549/291 |

*Primary Examiner*—C. Warren Ivy
*Assistant Examiner*—Raymond Covington
*Attorney, Agent, or Firm*—Ronald A. Daignault

[57] ABSTRACT

Novel lactone and lactam compounds which are useful to lower blood cholesterol levels in a patient, said compounds containing an arylcarboxamide or arylthiocarboxamide moiety.

10 Claims, No Drawings

SUBSTITUTED AMIDE ACAT INHIBITORS LACTONE DERIVATIVES

BACKGROUND OF THE INVENTION

This invention relates to chemical compounds having pharmacological activity, to pharmaceutical compositions which include these compounds, and to a pharmaceutical method of treatment. More particularly, this invention concerns certain lactone and lactam derivatives which inhibit the enzyme acyl-coenzyme A:-cholesterol acyltransferase (ACAT), pharmaceutical compositions containing these compounds, and a method of treating hypercholesterolemia and atherosclerosis. This invention also describes novel intermediates useful in preparing the pharmaceutically active compounds of this invention.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which would be effective in lowering total serum cholesterol levels. It is now known that cholesterol is transported in the blood in the form of complex particles consisting of a core of cholesteryl esters plus triglycerides and an exterior consisting primarily of phospholipids and a variety of types of protein which are recognized by specific receptors. For example, cholesterol is carried to the sites of deposit in blood vessels in the form of low density lipoprotein cholesterol (LDL cholesterol) and away from such sites of deposit by high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acyl-CoA:cholesterol transferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

SUMMARY OF THE INVENTION

Compounds of the following general Formula I have acyl coenzyme A:cholesterol acyltransferase (ACAT) inhibitory activity rendering them useful in lowering blood cholesterol levels.

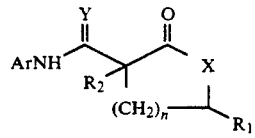

Formula I wherein n is an integer of from 1 to 3; wherein Y is oxygen or sulfur; wherein X is oxygen or N-R3; wherein R₁ is selected from
(a) hydrogen;
(b) a straight or branched saturated hydrocarbon chain having from 1 to 20 carbon atoms;
(c) A cycloalkyl group having from 3 to 6 carbon atoms;
(d) the group

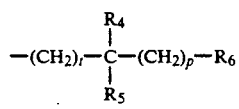

wherein t is zero to 4; p is zero to 4 with the proviso that the sum of t and p is not greater than 5; $R_4$ and $R_5$ are independently selected from hydrogen or alkyl having from 1 to 6 carbon atoms, or when $R_4$ is hydrogen, $R_5$ can be selected from the groups defined for $R_6$ and $R_6$ is phenyl or phenyl substituted with from 1 to 3 substituents selected from straight or branched alkyl having from 1 to 6 carbon atoms, straight or branched alkoxy having from 1 to 6 carbon atoms, straight or branched thioalkoxy having from 1 to 6 carbon atoms, phenoxy, hydroxy, nitro, trifluoromethyl, or $N_7R_8$ wherein $R_7$ and $R_8$ are the same or different and are hydrogen or alkyl of from 1 to 4 carbon atoms;
(e) phenyl or phenyl substituted with from 1 to 3 substituents selected from straight or branched alkyl having from 1 to 3 substituents selected from straight or branched alkyl having from 1 to 6 carbon atoms, straight or branched alkoxy having from 1 to 6 carbon atoms, straight or branched thioalkoxy having from 1 to 4 carbon atoms, phenoxy, hydroxy, nitro, trifluoromethyl, or $NR_7R_8$ wherein $R_7$ and $R_8$ have the meanings defined above;
(f) 2-, 3-, or 4-pyridyl;
wherein R₃ is selected from
(a) hydrogen;
(b) a straight or branched hydrocarbon chain having from 1 to 20 carbon atoms and which is saturated or contains from 1 to 3 double bonds; or
(c) phenyl or phenyl substituted with from 1 to 3 substituents selected from straight or branched alkyl having from 1 to 6 carbon atoms, straight or branched alkoxy having from 1 to 6 carbon atoms, straight or branched thioalkoxy having from 1 to 6 carbon atoms, phenoxy, hydroxy, nitro, trifluoromethyl, or $NR_7R_8$ wherein $R_7$ and $R_8$ have the meanings defined above;
wherein R₂ is hydrogen, a straight or branched alkyl group having from 1 to 6 carbon atoms, $-(CH_2)_m-Ph$ wherein m is an integer of from 1 to 3 and ph is phenyl optionally substituted with from 1 to substituents selected from straight or branched alkyl having from 1 to 4 carbon atoms, straight or branched alkoxy having from 1 to 4 carbon atoms; wherein Ar is selected from:

(a) phenyl which is unsubstituted or is substituted with from 1 to 3 substituents selected from
alkyl having from 1 to 6 carbon atoms and which is straight or branched,
alkoxy having from 1 to 6 carbon atoms and which is straight or branched,
phenoxy,
hydroxy,
fluorine,
chlorine,
bromine,
nitro,
trifluoromethyl,
—COOH,
—COOalkyl wherein alkyl has from 1 to 4 carbon atoms, or
—NR$_7$R$_6$ wherein R$_7$ and R$_8$ have the meanings defined above;

and pharmaceutically acceptable salts thereof.

Pharmaceutically acceptable salts of the compounds of Formula I are also included as a part of the present invention.

Also included within the scope of this invention are the open chain compounds formed by treatment of a compound of Formula I wherein X is oxygen with an alkali metal salt such as potassium hydroxide, sodium hydroxide, or lithium hydroxide.

The open chain compounds may be depicted by the following Formula II:

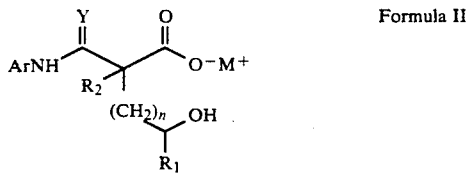

Formula II wherein Ar, n, Y, R$_1$, and R$_2$ have the meanings defined in Formula I and M represents an alkali metal.

Suitable acids for forming acid salts of the compounds of this invention containing a basic group include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The acid addition salts are formed by procedures well known in the art.

Certain compounds of the present invention may also exist in different stereoisomeric forms by virtue of the presence of asymmetric centers in the compound. The present invention contemplates all stereoisomeric forms of the compounds as well as mixtures thereof, including racemic mixtures. Individual stereoisomers may be obtained, if desired, by methods known in the art as, for example, the separation of stereoisomers in chiral chromatographic columns.

Further, the compounds of this invention may exist in unsolvated as well as solvated forms with pharmaceutically acceptable solvents such as water, ethanol, and the like. In general, the solvated forms are considered equivalent to the unsolvated forms for the purposes of this invention.

Illustrative examples of straight or branched saturated hydrocarbon chains having from 1 to 20 carbon atoms include methyl, ethyl, n-propyl, isopropyl, n-butyl, iso-butyl, tert-butyl, n-pentyl, isopentyl, n-hexyl, n-heptyl, n-octyl, n-undecyl, n-dodecyl, n-hexadecyl, 2,2-dimethyldodecyl, 2-ethyltetradecyl, and n-octadecyl groups.

Illustrative straight or branched hydrocarbon chains having from 1 to 20 carbon atoms and having from 1 to 3 double bonds are ethenyl, 2-propenyl, 2-butenyl, 3-pentenyl, 2-octenyl, 5-nonenyl, 4-undecenyl, 5-hepadecenyl, 3-octadecenyl, 9-octadecenyl, 2,2-dimethyl-11-eicosenyl, 9,12-octadecadienyl, and hexadecenyl.

Straight or branched alkoxy groups having from 1 to 6 carbon atoms include, for example, methoxy, ethoxy, n-propoxy, t-butoxy, and pentyloxy.

Illustrative of straight or branched alkyl groups having from 1 to 6 carbon atoms are methyl, ethyl, n-propyl, isopropyl, n-butyl, tert-butyl, pentyl, and hexyl.

Thioalkoxy means alkyl-S- wherein the alkyl moiety has from 1 to 6 carbon atoms and is straight or branched.

Preferred compounds of this invention include those of Formula I wherein Ar is phenyl disubstituted in the 2,6-positions. Also preferred are compounds wherein n is 1 or 2. Additional preferred compounds are those of Formula I wherein R$_1$ is a straight or branched saturated hydrocarbon chain having from 1 to 20 carbon atoms.

As shown by the data presented below in Table 1, the compounds of the present invention are potent inhibitors of the enzyme acyl-CoA: cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in F. J. Field and R. G. Salone, *Biochemica et Biophysica* 712:557-570 (1982). The test assesses the ability of a test compound to inhibit the acylation of cholesterol by oleic acid by measuring the amount of radiolabeled cholesterol oleate formed from radiolabeled oleic acid in a tissue preparation containing rabbit intestinal microsomes.

The data appear in Table 1 where they are expressed as IC$_{50}$ values; i.e., the concentration of test compound required to inhibit the activity of the enzyme by 50%.

TABLE 1

| Compound of Example | IC$_{50}$ (μM) |
|---|---|
| 1 | 0.587 |
| 2 | 0.26 |
| 3 | 0.404 |
| 4 | 0.336 |
| 7 | 1.33 |

The compounds may also be evaluated in an in vivo screen designated APCC whereby male Sprague-Dawley rats (200 to 225 g) are randomly divided into treatment groups and dosed at 4 PM with either vehicle (CMC/Tween) or suspensions of compounds in vehicle. The normal chow diet is then replaced with the PCC diet with either 1% or 0.5% cholic acid. The rats consume this diet ad libitum during the night and are sacrificed at 8 AM to obtain blood samples for cholesterol analysis using standard procedures. Statistical differences between mean cholesterol values for the same vehicle are determined using analysis of variance followed by Fisher's least significant test.

In therapeutic use as agents for treating hypercholesterolemia or atherosclerosis, the compounds of Formula I are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

Powders and tablets preferably contain between about 5% to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral administration, or suspensions and emulsions suitable for oral administration. Aqueous solutions for oral administration can be prepared by dissolving the active compound in water and adding suitable flavorants, colorings agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The compounds of this invention may be prepared as depicted in Chart I, Scheme A hereof. A lactone or lactam of Formula (A) wherein n, $R_1$, and X have the meanings defined in Formula I is treated with lithium diisopropylamide to form the lithio enolate which is treated with an appropriate isocyanate or thioisocyanate of the formula ArNCY to give compounds of Formula B. Treatment of compounds of Formula B with a base such as sodium hydride and alkylating with an appropriate agent of the formula $R_2X$ gives compounds of Formula I.

Synthesis of the lactone or lactam of Formula A is shown in Scheme B of Chart I. Generally the starting alcohol (1) is oxidized with pyridinium dichromate (PDC) in methylene chloride to give the corresponding aldehyde. Treatment of the aldehyde (2) with various Grignard reagents using standard reaction conditions yields the secondary alcohol (3) which can be cyclized using meta-chloroperbenzoic acid (m-CPBA) in methylene chloride to give the corresponding cyclic ether (4). The cyclic ether is treated with pyridinium chlorochromate (PCC) to give the lactone (5) (S. Chandrasekaran et al., Tet. Lett. 31, 2775 (1990)) which corresponds to Formula (A) wherein X is oxygen. Treatment of the lactone (5) with various alkoxides such as sodium alkoxide, RONa, wherein R is, e.g., an alkyl group, followed by oxidation and reductive amination give the lactam (7) which corresponds to Formula (A) wherein X is $N-R_3$. In Schemes A and B the various groups represented by n, $R_1$, $R_2$, X, Ar, Y, and $R_3$ are the same as defined in Formula I, halo is halogen, and B represents a base.

EXAMPLE 1

Preparation of
N-[2,6-bis(1-methylethyl)phenyl]-5-(4-fluorophenyl)tetrahydro-2-oxo-3-furancarboxamide To a cooled ($-78°$ C.) solution of diisopropylamine (1.40 g, 0.013 mol) in 90 mL ether, n-BuLi (0.013 mol) was added dropwise followed by 45 mL ether. After stirring for 5 minutes at $-78°$ C. under a nitrogen atmosphere, a solution of γ-(4-fluorophenyl)-γ-butyrolactone (2.50 g, 0.013 mol) in 23 mL ether was added dropwise and the resulting solution was stirred for 20 minutes at $-78°$ C. A solution of 2,6-diisopropylphenyl isocyanate in 23 mL ether was then added dropwise and the reaction mixture was allowed to gradually warm to room temperature and stir for 16 hours under a nitrogen atmosphere (J. F. Wolfe, et al, *Synthetic Communications* 17, 13 (1987)). The reaction mixture was then quenched with a saturated solution of ammonium chloride and extracted with methylene chloride. The layers were separated and the organic layer was washed two times with water, dried ($Na_2SO_4$) and concentrated in vacuo (30° C.) to afford a white residue. The residue was washed with hexane, filtered, and oven-dried (30° C.) to yield a white solid, 3.77 g (0.009 mol, 71.2%) of the title compound, mp 203°–205° C.

Analysis for $C_{23}H_{26}NO_3F$: Calcd: C, 72.03; H, 6.83; N, 3.65. Found: C, 72.16; H, 6.92; N, 3.88.

EXAMPLE 2

Preparation of
N-[2,6-bis(1-methylethyl)phenyl]-5-heptyltetrahydro-2-oxo-3-furancarboxamide The title compound, mp 95°–98° C., was prepared from undecanoic γ-lactone (5.0 g, 0.027 mol), 2,6-diisopropylphenyl isocyanate (5.50 g, 0.027 mol) and lithium diisopropylamide (0.027 mol) using the procedure described in Example 1.

Analysis for $C_{24}H_{37}NO_3$: Calcd: C, 74.37; H, 9.62; N, 3.61. Found: C, 74.05; H, 10.05; N, 3.97.

EXAMPLE 3

Preparation of
N-[2,6-bis(1-methylethyl)phenyl]-6-hexyltetrahydro-2-oxo-2H-pyran-3-carboxamide The title compound, mp 113°–115° C., was prepared from undecanoic acid δ-lactone (5.0 g, 0.027 mol), 2,6-diisopropylphenyl isocyanate (5.51 g, 0.027 mol), and lithium diisopropylamide (0.027 mol) using the procedure described in Example 1.

Analysis for $C_{24}H_{37}NO_3$: Calcd: C, 74.37; H, 9.62; N, 3.61. Found: C, 74.62; H, 10.02; N, 3.98.

EXAMPLE 4

Preparation of
N-[2,6-bis(1-methylethyl)phenyl]-6-heptyltetrahydro-2-oxo-2H-pyran-3-carboxamide The title compound was prepared from (±)-δ-dodecanolactone (5.0 g, 0.025 mol), 2,6-diisopropylphenyl isocyanate (5.12 g, 0.025 mol), and lithium diisopropylamide (0.025 mol) using the procedure described in Example 1.

MS: 401 (M+).

EXAMPLE 5

Preparation of
5-([1,1'-biphenyl]-4-yl)-N-[2,6-bis(1-methylethyl)-phenyl]tetrahydro-2-oxo-furancarboxamide The title compound was prepared from 5-(1,1'-biphenyl)-4-yldihydro-2(3H)-furanone (CAS Reg. No. 40885-19-6; 2.00 g, 0.008 mol), 2,6-diisopropylphenyl isocyanate (1.68 g, 0.008 mol) and lithium diisopropylamide (0.008 mol) using the procedure described in Example 1.

EXAMPLE 6

Preparation of
N-[2,6-bis(1-methylethyl)phenyl]-1-methyl-2-oxo-5-(3-pyridinyl)-3-pyrrolidinylcarboxamide The title compound was prepared from (−)-cotinine (5.0 g, 0.028 mol), 2,6-diisopropylphenyl isocyanate (5.69 g, 0.028 mol) and lithium diisopropylamide (0.028 mol) using the procedure described in Example 1.

EXAMPLE 7

Preparation of
γ-[2,6-bis(1-methylethyl)phenyl]-amino]carbonyl]-4-fluoro-α-hydroxybenzenebutanoic acid monosodium salt To a hot solution of N-[2,6-bis(1-methylethyl)-phenyl]-5-(4-fluorophenyl)tetrahydro-2-oxo-3-furancarboxamide (2.0 g, 0.005 mol for preparation see Example 1) in 35 mL methanol, 0.4 mL of 50% NaOH solution (1.0 eq) was added. After stirring for 4 hours at room temperature, this reaction mixture was concentrated in vacuo to afford the desired product, mp 183°–186° C.

Analysis for $C_{23}H_{27}FNNaO_4$: Calcd: C, 67.80; H, 6.68; N, 3.44. Found: C, 67.43; H, 6.70; N, 3.42.

EXAMPLE 8

Preparation of
N-[2,6-bis(1-methylethyl)phenyl-1-dodecylhexahydro-2-oxo-1H-azepine-3-carboxamide The title compound, mp 99-104° C., was prepared from 1 dodecylhexahydro-1-azacycloheptan-2-one-1-dodecyl-azone-2H-azepine-2-one (5.0 g, 0.017 mol, CAS Reg. N 59227-89-3, U.S. Pat. No. 3,989,816), 2,6-diisopropylphenyl isocyanate (3.61 g, 0.017 mol) and lithium diisopropylamide (0.017 mol) using the procedure described in Example 1.

EXAMPLE 9

Preparation of
N-[2,6-bis(1-methylethyl)phenyl]-1-dodecyl-2-oxo-3-pyrrolidine carboxamide The title compound was prepared from 1-dodecyl-2-pyrrolidinone (5.0 g, 0.019 mol), 2,6-diisopropylphenyl isocyanate (4.01 g, 0.019 mol) and lithium diisopropylamide (0.019 mol) using the procedure described in Example 1.

Analysis for $C_{29}H_{48}N_2O_2$: Calcd: C, 76.55; H, 10.71; N, 5.95. Found: C, 76.15; H, 10.56; N, 6.24.

CHART I

SCHEME A

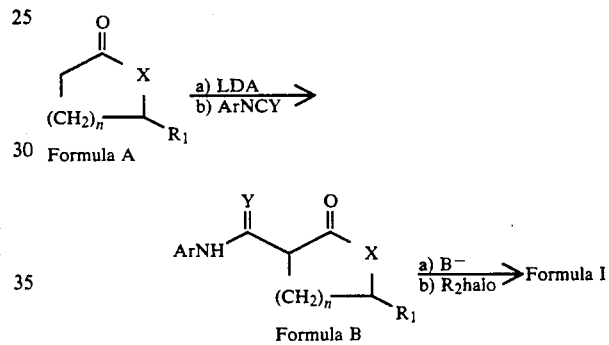

SCHEME B

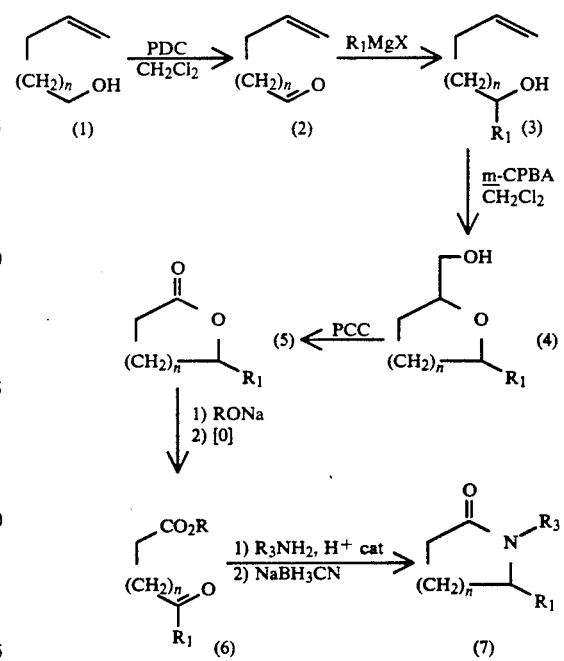

I claim:
1. A compound of Formula I or Formula II

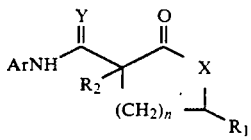

Formula I

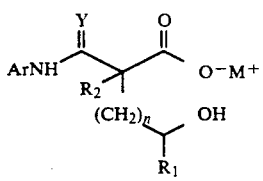

Formula II wherein n is an integer of from 1 to 3; wherein Y is oxygen or sulfur; wherein X is oxygen or N-$R_3$; wherein $R_1$ is selected from (a) hydrogen;

(b) a straight or branched saturated hydrocarbon chain having from 1 to 20 carbon atoms;

(c) A cycloalkyl group having from 3 to 6 carbon atoms;

(d) the group

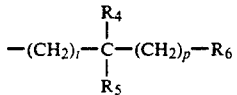

wherein t is zero to 4; p is zero to 4 with the proviso that the sum of t and p is not greater than 5; $R_4$ and $R_5$ are independently selected from hydrogen or alkyl having from 1 to 6 carbon atoms, or when $R_4$ is hydrogen, $R_5$ can be selected from the groups defined for $R_6$ and $R_6$ is phenyl or phenyl substituted with from 1 to 3 substituents selected from straight or branched alkyl having from 1 to 6 carbon atoms, straight or branched alkoxy having from 1 to 6 carbon atoms, straight or branched thioalkoxy having from 1 to 6 carbon atoms, phenoxy, hydroxy, nitro, trifluoromethyl, or $NR_7R_8$ wherein $R_7$ and $R_8$ are the same or different and are hydrogen or alkyl of from 1 to 4 carbon atoms;

(e) phenyl or phenyl substituted with from 1 to 3 substituents selected from straight or branched alkyl having from 1 to 3 substituents selected from straight or branched alkyl having from 1 to 6 carbon atoms, straight or branched alkoxy having from 1 to 6 carbon atoms, straight or branched thioalkoxy having from 1 to 4 carbon atoms, phenoxy, hydroxy, nitro, trifluoromethyl, or $NR_7R_8$ wherein $R_7$ and $R_8$ have the meanings defined above;

(f) 2-, 3-, or 4-pyridyl;

wherein $R_3$ is selected from (a) hydrogen;

(b) a straight or branched hydrocarbon chain having from 1 to 20 carbon atoms and which is saturated or contains from 1 to 3 double bonds; or (c) phenyl or phenyl substituted with from 1 to 3 substituents selected from straight or branched alkyl having from 1 to 6 carbon atoms, straight or branched alkoxy having from 1 to 6 carbon atoms, straight or branched thioalkoxy having from 1 to 6 carbon atoms, phenoxy, hydroxy, nitro, trifluoromethyl, or $NR_7R_8$ wherein $R_7$ and $R_8$ have the meanings defined above;

wherein $R_2$ is hydrogen, a straight or branched alkyl group having from 1 to 6 carbon atoms, —$(CH_2)_m$—Ph wherein m is an integer of from 1 to 3 and Ph is phenyl optionally substituted with from 1 to 3 substituents selected from straight or branched alkyl having from 1 to 4 carbon atoms, straight or branched alkoxy having from 1 to 4 carbon atoms;

wherein Ar is selected from:

(a) phenyl which is unsubstituted or is substituted with from 1 to 3 substituents selected from alkyl having from 1 to 6 carbon atoms and which is straight or branched, alkoxy having from 1 to 6 carbon atoms and which is straight or branched, phenoxy, hydroxy, fluorine, chlorine, bromine, nitro, trifluoromethyl,

—COOH,

—COOalkyl wherein alkyl has from 1 to 4 carbon atoms, or

—$NR_7R_8$ wherein $R_7$ and $R_8$ have the meanings defined above;

wherein M+ is an alkali metal cation and pharmaceutically acceptable salts thereof.

2. A compound of claim 1 wherein Y is oxygen.

3. A compound of claim 2 wherein $R_2$ is hydrogen.

4. A compound of claim 4 wherein n is one or two.

5. A compound of claim 4 wherein Ar is phenyl substituted with alkyl having from 1 to 6 carbon atoms and which is straight or branched.

6. A compound of claim 5 wherein the alkyl groups are on the 2 and 6 positions of the phenyl ring.

7. A compound of claim 6 which is

N-[2,6-bis(1-methylethyl)phenyl]-5-(4-fluorophenyl)tetrahydro-2-oxo-3-furancarboxamide;

N-[2,6-bis(1-methylethyl)phenyl]-5-heptyltetrahydro-2-oxo-3-furancarboxamide;

N-[2,6-bis(1-methylethyl)phenyl]-6-hexyltetrahydro-2-oxo-2H-pyran-3-carboxamide;

N-[2,6-bis(1-methylethyl)phenyl]-6-heptyltetrahydro-2-oxo-2H-pyran-3-carboxamide; or 5-([1,1'-biphenyl]-4-yl)-N-[2,6-bis(1-methylethyl)-phenyl]tetrahydro-2-oxo-3-furancarboxamide.

8. A compound of claim 1 wherein $R_1$ is a straight or branched saturated hydrocarbon chain having from 1 to 20 carbon toms.

9. A pharmaceutical composition which comprises a compound of claim 1 and a pharmaceutically acceptable carrier.

10. A method of lowering the blood cholesterol in a patient in need thereof which comprises administering to said patient an effective amount of a compound of claim 1.

* * * * *

UNITED STATES PATENT AND TRADEMARK OFFICE
CERTIFICATE OF CORRECTION

PATENT NO. : 5,185,349
DATED : Feb. 9, 1993
INVENTOR(S) : Augelli-Szafran

It is certified that error appears in the above-indentified patent and that said Letters Patent is hereby corrected as shown below:

Column 8, line 67, delete "or Formula II"

Column 9, lines 8-14, delete structure and Formula II

Column 9, line 17, delete "or N-$R_3$"

Column 9, delete lines 56-63 to Column 10, lines 1-5

Column 10, line 32, delete "wherein M+ is an alkali metal cation"

Column 10, claim 4, line 36, replace "4" with --3--

Column 10, line 55, delete "toms" and insert instead --atoms--

Signed and Sealed this

Nineteenth Day of April, 1994

Attest:

BRUCE LEHMAN

*Attesting Officer*     *Commissioner of Patents and Trademarks*